United States Patent
Thuppanna et al.

(10) Patent No.: US 12,386,811 B2
(45) Date of Patent: *Aug. 12, 2025

(54) METHOD, APPARATUS, AND COMPUTER PROGRAM PRODUCT FOR IMPROVED TRACKING OF STATE DATA

(71) Applicant: HealthStream, Inc., Nashville, TN (US)

(72) Inventors: Nataraja Thuppanna, Morrisville, NC (US); Ismael Cruz, Durham, NC (US); Debora Sinclair, Durham, NC (US)

(73) Assignee: HealthStream, Inc., Nashville, TN (US)

( * ) Notice: Subject to any disclaimer, the term of this patent is extended or adjusted under 35 U.S.C. 154(b) by 141 days.

This patent is subject to a terminal disclaimer.

(21) Appl. No.: 17/163,078

(22) Filed: Jan. 29, 2021

(65) Prior Publication Data

US 2021/0149870 A1 May 20, 2021

Related U.S. Application Data

(63) Continuation of application No. 15/597,403, filed on May 17, 2017, now Pat. No. 10,936,572.

(51) Int. Cl.
*G06F 16/00* (2019.01)
*G06F 16/17* (2019.01)
(Continued)

(52) U.S. Cl.
CPC .......... *G06F 16/23* (2019.01); *G06F 16/1727* (2019.01); *G06F 16/21* (2019.01);
(Continued)

(58) Field of Classification Search
CPC .... G06F 16/23; G06F 16/1727; G06F 16/958; G06F 16/2379; G06F 16/2308;
(Continued)

(56) References Cited

U.S. PATENT DOCUMENTS 6,301,585 B1 10/2001 Milne
6,366,954 B1 4/2002 Traversat et al.
(Continued)

FOREIGN PATENT DOCUMENTS

EP 3026583 A1 * 6/2016
EP 3438846 B1 * 7/2022
WO WO2009042941 A1 * 4/2009

OTHER PUBLICATIONS

Benoit Dageville et al., "The Snowflake Elastic Data Warehouse", SIGMOD '16: Proceedings of the 2016 International Conference on Management of Data Jun. 2016, pp. 215-226.*
(Continued)

*Primary Examiner* — Srirama Channavajjala
(74) *Attorney, Agent, or Firm* — André J. Bahou; Bradley Arant Boult Cummings LLP

(57) ABSTRACT

A method, apparatus, and computer program product is provided for tracking state data of objects during a session, and saving the data to a database. The tracking may be performed by a reusable set of computer program code accessible by a plurality of user interface applications. Temporary data may be stored as insert objects, update objects, and delete objects and maintained during a session of a user interface application. The temporary data may be updated as additional data is manipulated by the user interface application, but does not need to be tracked by the user interface application. The user interface application indicates if data is to be deleted, or is current (e.g., new or modified). Upon completion of the session, calls are made to update the database based on the temporary data.

15 Claims, 3 Drawing Sheets

(51) Int. Cl.
*G06F 16/21* (2019.01)
*G06F 16/23* (2019.01)
*G06F 16/27* (2019.01)
*G06F 16/951* (2019.01)
*G06F 16/958* (2019.01)
*G16H 10/60* (2018.01)

(52) U.S. Cl.
CPC ...... *G06F 16/2308* (2019.01); *G06F 16/2379* (2019.01); *G06F 16/27* (2019.01); *G06F 16/951* (2019.01); *G06F 16/958* (2019.01); *G16H 10/60* (2018.01)

(58) Field of Classification Search
CPC ........ G06F 16/951; G06F 16/27; G06F 16/21; G16H 10/60
See application file for complete search history.

(56) References Cited

U.S. PATENT DOCUMENTS

| | | | |
|---|---|---|---|
| 6,493,695 B1 | 12/2002 | Pickering et al. | |
| 6,553,392 B1* | 4/2003 | Mosher, Jr. | G06F 11/2082 |
| | | | 714/E11.107 |
| 6,553,405 B1 | 4/2003 | Desrochers | |
| 6,598,057 B1 | 7/2003 | Synnestvedt et al. | |
| 7,209,970 B1 | 4/2007 | Everson et al. | |
| 7,689,565 B1* | 3/2010 | Gandhi | G06F 16/27 |
| | | | 707/999.01 |
| 7,814,124 B1 | 10/2010 | De Jong et al. | |
| 7,904,487 B2 | 3/2011 | Ghatare | |
| 8,352,424 B2 | 1/2013 | Zunger et al. | |
| 8,782,736 B1 | 7/2014 | Thuppanna et al. | |
| 8,821,294 B2* | 9/2014 | McCaffrey | A63F 9/24 |
| | | | 463/42 |
| 8,910,184 B2 | 12/2014 | Dixon et al. | |
| 9,253,154 B2* | 2/2016 | Gaitonde | H04L 63/0245 |
| 9,798,759 B2* | 10/2017 | Schreter | G06F 16/2308 |
| 9,940,403 B2 | 4/2018 | Chow et al. | |
| 2002/0147857 A1 | 10/2002 | Sanchez et al. | |
| 2003/0074227 A1 | 4/2003 | Yu | |
| 2003/0195904 A1* | 10/2003 | Chestnut | G06F 21/6227 |
| 2003/0200212 A1* | 10/2003 | Benson | G06F 9/466 |
| 2004/0139107 A1* | 7/2004 | Bachman | G06F 16/951 |
| 2004/0244012 A1 | 12/2004 | Massarenti | |
| 2006/0123046 A1 | 6/2006 | Doise et al. | |
| 2006/0218538 A1 | 9/2006 | Van Kesteren | |
| 2006/0277220 A1 | 12/2006 | Patrick et al. | |
| 2006/0282460 A1 | 12/2006 | Pandya et al. | |
| 2007/0237086 A1* | 10/2007 | Tulac | G06F 16/2477 |
| | | | 370/244 |
| 2007/0239751 A1 | 10/2007 | Wei et al. | |
| 2007/0239798 A1* | 10/2007 | Shringi | G06F 16/2365 |
| 2007/0294308 A1* | 12/2007 | Megerian | G06F 16/21 |
| 2009/0037446 A1 | 2/2009 | Tonev et al. | |
| 2010/0049745 A1 | 2/2010 | Aebig et al. | |
| 2010/0050230 A1 | 2/2010 | Aebig et al. | |
| 2010/0191712 A1* | 7/2010 | Wolman | G06F 16/2379 |
| | | | 707/704 |
| 2011/0196830 A1 | 8/2011 | Zunger et al. | |
| 2012/0078432 A1 | 3/2012 | Weatherhead et al. | |
| 2013/0111499 A1 | 5/2013 | Dixon et al. | |
| 2013/0117326 A1 | 5/2013 | De et al. | |
| 2013/0124667 A1 | 5/2013 | Chow et al. | |
| 2013/0191420 A1 | 7/2013 | Petri et al. | |
| 2013/0318117 A1 | 11/2013 | Abdul et al. | |
| 2014/0068423 A1* | 3/2014 | Nakashima | G06F 40/169 |
| | | | 715/243 |
| 2014/0075501 A1 | 3/2014 | Srinivasan et al. | |
| 2014/0229947 A1* | 8/2014 | Daudel | G06F 11/3636 |
| | | | 718/1 |
| 2014/0304825 A1 | 10/2014 | Gianniotis et al. | |
| 2015/0052108 A1* | 2/2015 | Volk | G06F 11/1446 |
| | | | 707/649 |
| 2015/0088815 A1* | 3/2015 | Billapati | G06F 16/21 |
| | | | 707/609 |
| 2015/0142854 A1 | 5/2015 | Seth et al. | |
| 2016/0094681 A1 | 3/2016 | Wu | |
| 2017/0076740 A1 | 3/2017 | Feast et al. | |
| 2017/0103127 A1* | 4/2017 | Hanson | G06F 16/958 |
| 2017/0293668 A1 | 10/2017 | Crabtree et al. | |
| 2018/0018428 A1* | 1/2018 | Coifman | G06F 16/27 |

OTHER PUBLICATIONS

Bi Li, Wenxuan Xie et al., "Learning to Update for Object Tracking With Recurrent Meta-Learner", IEEE Transactions on Image Processing, vol. 28, No. 7, Jul. 2019, pp. 3624.*
"Advanced Claim Management," Change Healthcare, www.changehealthcare.com/solutions/medical-network/advanced-claim-management, last accessed Jun. 28, 2021.
"Ahi QA and Ahi Lobby," Change Healthcare, www.changehealthcare.com/solutions/revenue-cycle-management/patient-access-financial-clearance/ahi-qa-ahi-lobby, last accessed Jun. 28, 2021.
"API & Services Connection for Healthcare," Change Healthcare, www.changehealthcare.com/solutions/medical-network/api-services-connection, last accessed Jun. 28, 2021.
"Change Healthcare Cardiology Analytics," Change Healthcare, www.changehealthcare.com/solutions/enterprise-imaging/cardiology/analytics, last accessed Jun. 28, 2021.
"Change Healthcare Cardiology Cath," Change Healthcare, www.changehealthcare.com/solutions/enterprise-imaging/cardiology/cath, last accessed Jun. 28, 2021.
"Change Healthcare Cardiology Charge Manager," Change Healthcare, www.changehealthcare.com/solutions/enterprise-imaging/cardiology/charge-manager, last accessed Jun. 28, 2021.
"Change Healthcare Cardiology ECG Management," Change Healthcare, www.changehealthcare.com/solutions/enterprise-imaging/cardiology/ecg-management, last accessed Jun. 28, 2021.
"Change Healthcare Cardiology EP Solutions," Change Healthcare, www.changehealthcare.com/solutions/enterprise-imaging/cardiology/ep-solutions, last accessed Jun. 28, 2021.
"Change Healthcare Cardiology Hemo," Change Healthcare, www.changehealthcare.com/solutions/enterprise-imaging/cardiology/hemo, last accessed Jun. 28, 2021.
"Change Healthcare Cardiology Nuclear Medicine Advanced Visualization," Change Healthcare, www.changehealthcare.com/solutions/enterprise-imaging/cardiology/nuclear-medicine-advanced-visualization, last accessed Jun. 28, 2021.
"Change Healthcare Enterprise Imaging Network Archive," Change Healthcare, www.changehealthcare.com/solutions/enterprise-imaging/enterprise-imaging-network/archive, last accessed Jun. 28, 2021.
"Change Healthcare Enterprise Viewer," Change Healthcare, www.changehealthcare.com/solutions/enterprise-imaging/enterprise-viewer, last accessed Jun. 28, 2021.
"Change Healthcare Image Repository," Change Healthcare, www.changehealthcare.com/solutions/enterprise-imaging/image-repository, last accessed Jun. 28, 2021.
"Change Healthcare Imaging Fellow," Change Healthcare, www.changehealthcare.com/solutions/enterprise-imaging/imaging-fellow, last accessed Jun. 28, 2021.
"Change Healthcare Imaging Share," Change Healthcare, www.changehealthcare.com/solutions/enterprise-imaging/imaging-share, last accessed Jun. 28, 2021.
"Change Healthcare Mammography Plus," Change Healthcare, www.changehealthcare.com/solutions/enterprise-imaging/radiology/mammography-plus, last accessed Jun. 28, 2021.
"Change Healthcare Radiology Collaboration," Change Healthcare, www.changehealthcare.com/solutions/enterprise-imaging/radiology/collaboration, last accessed Jun. 28, 2021.
"Change Healthcare Radiology Solutions," Change Healthcare, www.changehealthcare.com/solutions/enterprise-imaging/radiology/radiology-solutions, last accessed Jun. 28, 2021.
"Change Healthcare Study Share," Change Healthcare, www.changehealthcare.com/solutions/enterprise-imaging/radiology/study-share, last accessed Jun. 28, 2021.

(56) References Cited

OTHER PUBLICATIONS

"Change Healthcare Workflow Intelligence," Change Healthcare, www.changehealthcare.com/solutions/enterprise-imaging/workflow-intelligence, last accessed Jun. 28, 2021.
"Claiming & Remittance," Change Healthcare, www.changehealthcare.com/solutions/medical-network/claiming-remittance, last accessed Jun. 28, 2021.
"Claims Automation," Change Healthcare, www.changehealthcare.com/solutions/medical-network/claims-automation, last accessed Jun. 28, 2021.
"ConnectCenter," Change Healthcare, www.changehealthcare.com/solutions/medical-network/connectcenter, last accessed Jun. 28, 2021.
"Credentialing Advocate Solution," Change Healthcare, www.changehealthcare.com/solutions/dental-network/credentialing-advocate, last accessed Jun. 28, 2021.
"Dental Claim Attachments," Change Healthcare, www.changehealthcare.com/solutions/dental-network/dental-claim-attachments, last accessed Jun. 28, 2021.
"Dental Practice Analytic Insights," Change Healthcare, www.changehealthcare.com/solutions/dental-network/dental-practice-analytic-insights, last accessed Jun. 28, 2021.
"Enterprise Business Insight," Change Healthcare, www.changehealthcare.com/solutions/revenue-cycle-management/revenue-cycle-analytics/enterprise-business-insight, last accessed Jun. 28, 2021.
"Enterprise Imaging Network Analytics," Change Healthcare, www.changehealthcare.com/solutions/enterprise-imaging/enterprise-imaging-network/analytics, last accessed Jun. 28, 2021.
"Enterprise Pharmacy System," Change Healthcare, www.changehealthcare.com/solutions/pharmacy/management/enterprise-pharmacy-system, last accessed Jun. 28, 2021.
"Imaging Optimization," Change Healthcare, www.changehealthcare.com/solutions/enterprise-imaging/medical-imaging-consulting/imaging-optimization, last accessed Jun. 28, 2021.
"InterQual Evidence-Based Development," Change Healthcare, www.changehealthcare.com/solutions/clinical-decision-support/interqual/evidence-based-development, last accessed Jun. 28, 2021.
"Medical Claim Attachments," Change Healthcare, www.changehealthcare.com/solutions/medical-network/medical-claim-attachments, last accessed Jun. 28, 2021.
"Part D Complete & Community Advocate," Change Healthcare, www.changehealthcare.com/solutions/eligibility-enrollment/part-d-complete-community-advocate, last accessed Jun. 28, 2021.
"Payer Connectivity Services," Change Healthcare, www.changehealthcare.com/solutions/medical-network/payer-connectivity-services, last accessed Jun. 28, 2021.
SoftwareArtist, Read and Write JSON with Python, 2015, gowrishankarnath.com (Year: 2015).

\* cited by examiner

METHOD, APPARATUS, AND COMPUTER PROGRAM PRODUCT FOR IMPROVED TRACKING OF STATE DATA

TECHNOLOGICAL FIELD

Embodiments of the present invention relate generally to computer technology and, more particularly, to methods, apparatuses, and computer program products for improved tracking of state data in a session.

BACKGROUND

Many web based systems and services provide user interfaces for users to enter data, manipulate the data, and perform various user configurations to enable the web application to function as intended by the user. Many of the interfaces span multiple pages, some of which are dependent on user inputs made to fields on previous pages.

Data displayed by the applications is often retrieved from a database, and configurations of the data and new data records are transmitted to the database as directed by the user. In some systems, web applications update the database as the data is provided and retrieve data from the database as it is requested, resulting in near real-time updates to the database. However, numerous applications and users may access the data at a given time, and this approach could result in a large number of calls to the database. Some systems could therefore experience performance issues, including at the server and/or database level, due to the high volume of expensive database operations.

As an alternative to making calls to the database on an as-needed basis, some web applications could track the data in the user interface application. However, the data provided by the user could result in cumbersome state tracking in the user interface portion of the application while the user navigates throughout the application and continues to manipulate the data. This approach would require extensive configuration and programming by application developers to track the data in each user interface application until the session is complete and the data can be transmitted to the database.

BRIEF SUMMARY

Methods, apparatuses, and computer program products are therefore provided for improved tracking of state data in a session. Example embodiments provide a reusable interface such that various applications can access the interface and reuse the interface to handle the maintenance of data based on the user inputs provided during the session. When the user interface application indicates the data configuration is complete, example embodiments transmit the necessary calls to the database to provide the committed updates, additions, and deletions to the database. Example embodiments may therefore minimize or reduce the number of database operations in comparison to alternative implementations and further reduce the application code needed to be written by developers of applications that would otherwise be needed to track the state of data within the user interface application.

A method is provided for tracking state data of objects during a session for updating a database. The method comprises receiving an indication of a user interface operation based on a user input to a user interface, processing the user interface operation to generate temporary data, wherein the temporary data is categorized as at least one of an insert object, update object or delete object. The method further includes updating the temporary data according to subsequently received indications of user interface operations, receiving a commit indication indicating to commit the user interface operations to the database, and in response to the commit indication, transmitting data referenced by the temporary data to the database with operations associated with each of the respective insert objects, update objects and delete objects.

In some embodiments, the tracking of the state data is performed by a reusable set of computer program instructions configured as an application program interface (API) compatible with a plurality of object types and a plurality of database tables.

In some embodiments, processing the user interface operation comprise, in an instance the user interface operation indicates NewOrModified, and a referenced object comprises a record identifier, adding an associated reference as an update object. Processing the user interface operation may further comprise, in an instance the user interface operation indicates the referenced object is NewOrModified, and the referenced object does not comprise a unique record identifier, determining whether the referenced object is referenced in the temporary data and maintaining the temporary data accordingly.

The method may therefore also include, in an instance the user interface operation indicates the referenced object is NewOrModified, the referenced object does not comprise a unique record identifier, and the referenced object is referenced in the temporary data, preventing duplicate references from being added to the temporary data.

Further, the method may include, in an instance the user interface operation indicates the referenced object is NewOrModified, the referenced object does not comprise a unique record identifier, and the referenced object is not referenced in the temporary data, adding an insert object to the temporary data, wherein the insert object includes a reference to the referenced object as indicated by the user interface operation.

In some embodiments, transmitting the data referenced by the temporary data to the database comprises minimizing a number of database calls.

The method may further include maintaining a map that maps record identifiers recognizable by the database to associated objects in the temporary data.

The user interface operation indicates referenced data is either (a) NewOrModified, or (b) Deleted. The user interface operation may indicate the referenced data is NewOrModified, but does not distinguish whether the referenced data is new or modified.

An apparatus is provided for tracking state data of objects during a session for updating a database. The apparatus comprises at least one processor and at least one memory including computer program code, the at least one memory and the computer program code configured to, with the processor, cause the apparatus to at least receive an indication of a user interface operation based on a user input to a user interface, and process the user interface operation to generate temporary data, wherein the temporary data is categorized as at least one of an insert object, update object or delete object. The memory and computer program code may be further configured to update the temporary data according to subsequently received indications of user interface operations and receive a commit indication indicating to commit the user interface operations to the database. The memory and computer program code may be further configured to, in response to the commit indication, transmit data referenced by the temporary data to the database with operations associated with each of the respective insert objects, update objects and delete objects.

A computer program product is provided for tracking state data of objects during a session for updating a database. The computer program product comprises at least one non-transitory computer-readable storage medium having computer-executable program code instructions stored therein, the computer-executable program code instructions comprising program code instructions to receive an indication of a user interface operation based on a user input to a user interface and process the user interface operation to generate temporary data, wherein the temporary data is categorized as at least one of an insert object, update object or delete object. The computer-executable program code instructions may further comprise program code instructions to update the temporary data according to subsequently received indications of user interface operations, receive a commit indication indicating to commit the user interface operations to the database, and in response to the commit indication, transmit data referenced by the temporary data to the database with operations associated with each of the respective insert objects, update objects and delete objects.

An apparatus is provided with means for tracking state data of objects during a session for updating a database. The apparatus further comprises means for receiving an indication of a user interface operation based on a user input to a user interface, means for processing the user interface operation to generate temporary data, wherein the temporary data is categorized as at least one of an insert object, update object or delete object. The apparatus further includes means for updating the temporary data according to subsequently received indications of user interface operations, means for receiving a commit indication indicating to commit the user interface operations to the database, and in response to the commit indication, means for transmitting data referenced by the temporary data to the database with operations associated with each of the respective insert objects, update objects and delete objects.

The above summary is provided merely for purposes of summarizing some example embodiments of the invention so as to provide a basic understanding of some aspects of the invention. Accordingly, it will be appreciated that the above described example embodiments are merely examples and should not be construed to narrow the scope or spirit of the disclosure in any way. It will be appreciated that the scope of the disclosure encompasses many potential embodiments, some of which will be further described below, in addition to those here summarized.

BRIEF DESCRIPTION OF THE SEVERAL VIEWS OF THE DRAWINGS

Figure 1:
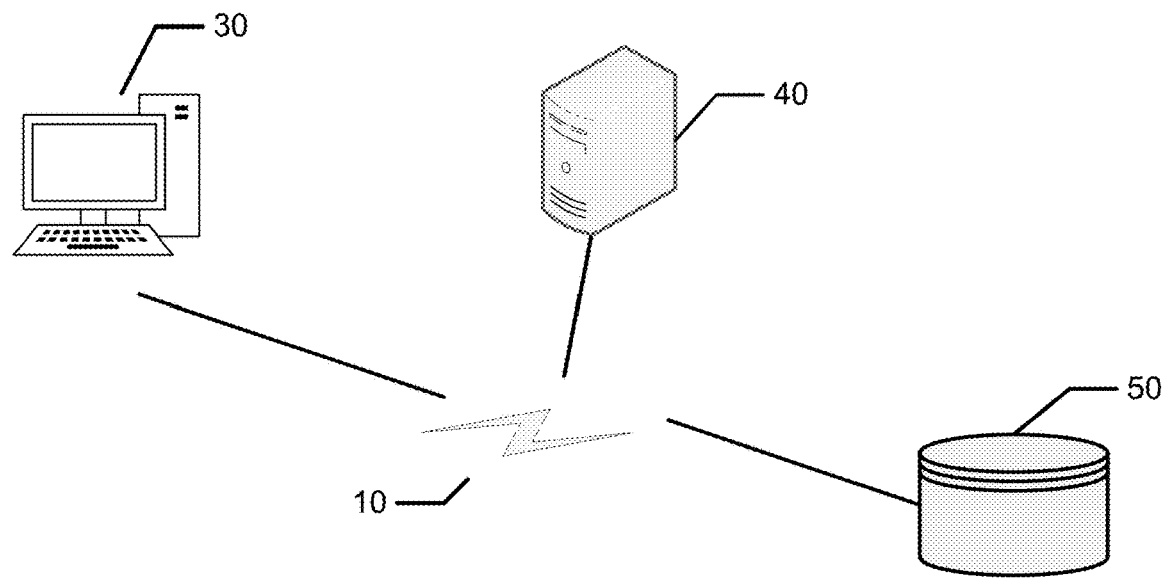
Figure 2:
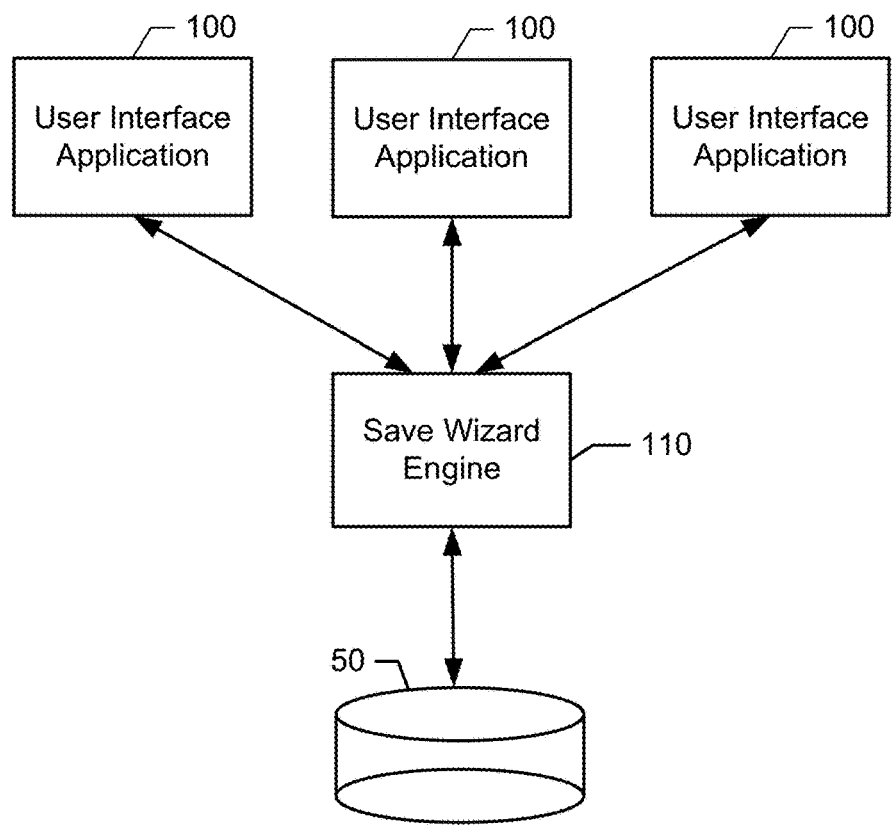
Figure 3:
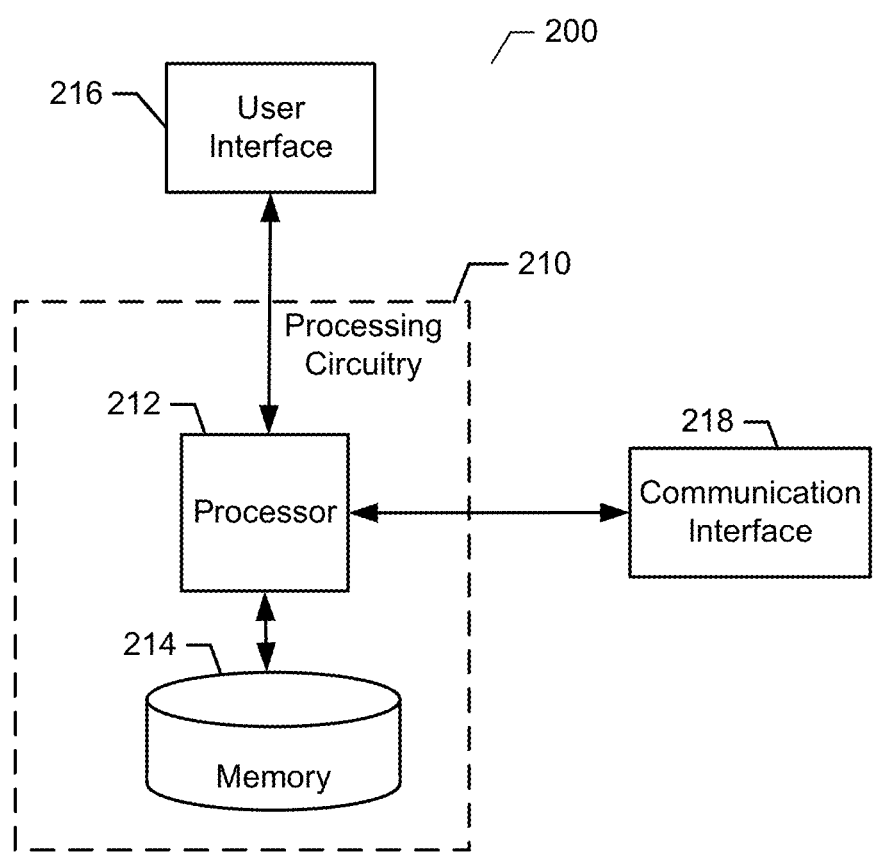
Figure 4:
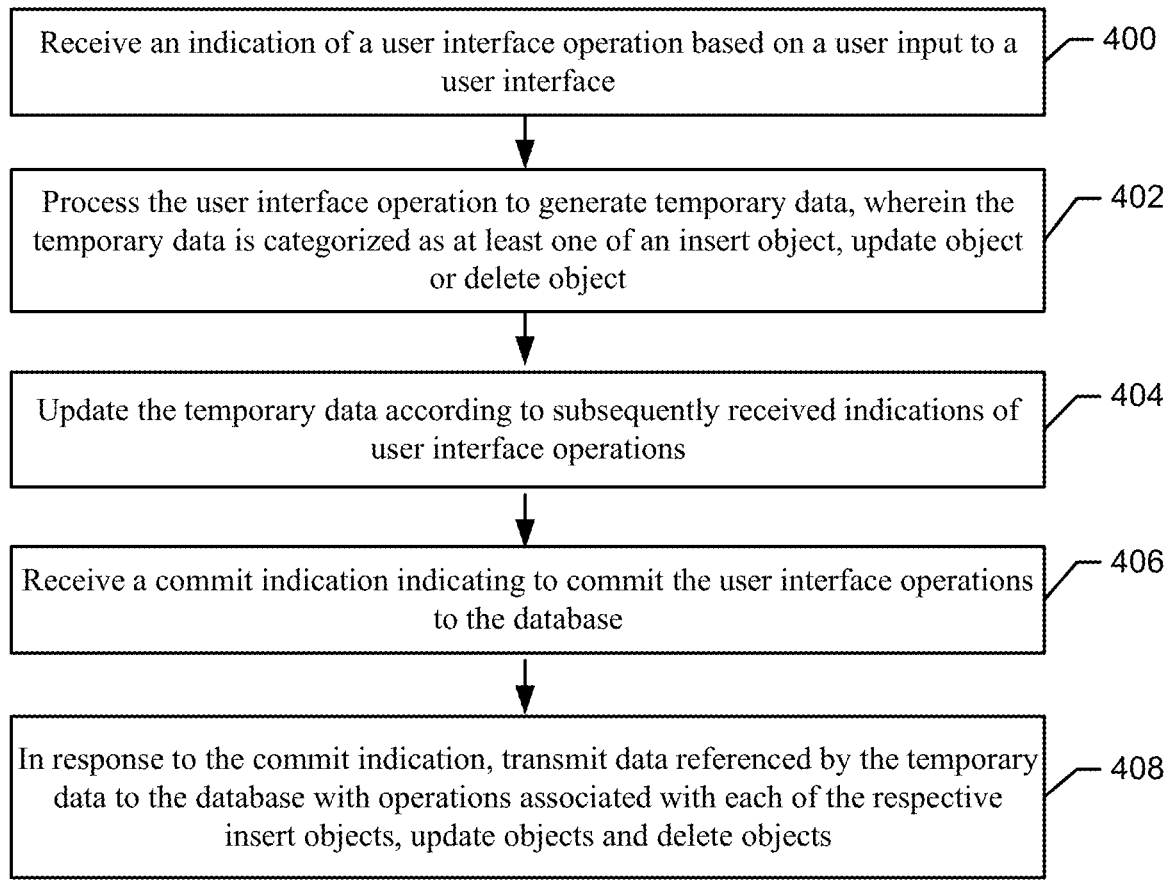

Having thus described embodiments of the invention in general terms, reference will now be made to the accompanying drawings, which are not necessarily drawn to scale, and wherein:

FIGS. 1 and 2 are overviews of example systems that can be used to practice some example embodiments described herein;

FIG. 3 is a schematic diagram of an apparatus in accordance with some example embodiments; and FIG. 4 is a flowchart of operations that may be performed in accordance with some example embodiments.

DETAILED DESCRIPTION

Some embodiments of the present invention will now be described more fully hereinafter with reference to the accompanying drawings, in which some, but not all embodiments of the invention are shown. Indeed, various embodiments of the invention may be embodied in many different forms and should not be construed as limited to the embodiments set forth herein; rather, these embodiments are provided so that this disclosure will satisfy applicable legal requirements. Like reference numerals refer to like elements throughout.

As used herein, where a computing device is described herein to receive data from another computing device, it will be appreciated that the data may be received directly from the other computing device and/or may be received indirectly via one or more intermediary computing devices, such as, for example, one or more servers, relays, routers, network access points, and/or the like. Similarly, where a computing device is described herein to transmit data to other computing devices, it will be appreciated that the data may be sent directly to the other computing device or may be sent to the other computing device via one or more interlinking computing devices, such as, for example, one or more servers, relays, routers, network access points, and/or the like.

FIG. 1 is an overview of a system that can be used to practice certain embodiments described herein, and should not be considered limiting. As illustrated in FIG. 1, example embodiments may be implemented as or employed in a distributed system. The various depicted components may be configured to communicate over a network 10, such as the Internet, for example, or any other communication interface as described in further detail hereinafter. In general, client device(s) 30 may be configured to communicate with a server 40 and/or database 50. Client device 30 may include any computing device such as a personal computer, laptop, smart phone, tablet, and/or the like. In some examples, any number of user devices 30 may be configured to communicate with server 40, which may be configured to host applications, process requests from the client device 30, provide data and content to the client device 30, and/or the like. The server 40 may be communicatively connected to database 50 which may be configured to store data, content, and/or the like. The client device 30, server 40 and/or database 50 may be configured to perform any of the operations described herein.

FIG. 2 is another overview of a system that can be used to practice certain embodiments described herein. As shown, multiple different user interface applications 100 may communicate with save wizard engine 110 to perform tracking of state data of objects manipulated by the respective user interface applications 100 during a session, and to save the data to the database 50.

The user interface applications 100 may generate objects for display by a browser or other similar application and allow the user to manipulate the data. The save wizard engine 110 may track the data manipulated by the user interface application 100 during a session, and save the relevant data to the database 50 when the session is complete. The save wizard engine 110 may therefore be implemented in a middle tier of a multi-tier architecture such that the save wizard engine 110 facilitates communication between a data-tier layer (e.g., database 50) and the user interface applications 100. In some examples, the user interface applications 100 and save wizard engine 110 may be implemented on server 40. As another example, the user interface applications 100 and save wizard engine 110 may be implemented on various servers 40 configured to operate as a distributed system.

Any of the operations described herein, such as those described with respect to FIG. 4, may be at least partially implemented as a reusable set of computer program instructions compatible with a plurality of object types. Any of the operations described herein may be provided by the save wizard engine 110 via an Application Program Interface (API) configured for reuse by a user interface application 100, including user interface applications to be developed in the future. As additional user interface applications are implemented, such as on server 40, and/or as additional database tables are added to database 50, the API provided by example embodiments may continue to be utilized by application developers to track the state data during a session for subsequent saving to the database. Example embodiments therefore may minimize or reduce the application development needed to track the state data in each of the user interface applications.

The systems of FIGS. 1 and 2 described above are provided merely as example implementations and it will be appreciated that the example embodiments provided herein may be implemented as or employed by any number of system architectures.

Referring now to FIG. 3, apparatus 200 is a computing device(s) configured according to example embodiments for improved tracking of state data in a session. Apparatus 200 may at least partially or wholly embody any of the network 10, client device 30, server 40, database 50, user interface applications 100, and/or save wizard engine 110 described above. Apparatus 200 may therefore implement any of the network 10, client device 30, server 40, database 50, user interface applications 100, and/or save wizard engine 110, in accordance with some example embodiments, or may be implemented as a distributed system that includes any of the network 10, client device 30, server 40, database 50, user interface applications 100, and/or save wizard engine 110.

It should be noted that the components, devices, and elements illustrated in and described with respect to FIG. 3 below may not be mandatory and thus some may be omitted in certain embodiments. For example, FIG. 3 illustrates a user interface 216, as described in more detail below, which may be optional in the server 40, database 50, and/or save wizard engine 110. Additionally, some embodiments may include further or different components, devices, or elements beyond those illustrated in and described with respect to FIG. 3.

Continuing with FIG. 3, processing circuitry 210 may be configured to perform actions in accordance with one or more example embodiments disclosed herein. In this regard, the processing circuitry 210 may be configured to perform and/or control performance of one or more functionalities of apparatus 200 in accordance with various example embodiments. The processing circuitry 210 may be configured to perform data processing, application execution, and/or other processing and management services according to one or more example embodiments. In some embodiments apparatus 200, or a portion(s) or component(s) thereof, such as the processing circuitry 210, may be embodied as or comprise a circuit chip. The circuit chip may constitute means for performing one or more operations for providing the functionalities described herein.

In some example embodiments, the processing circuitry 210 may include a processor 212, and in some embodiments, such as that illustrated in FIG. 3, may further include memory 214. The processing circuitry 210 may be in communication with or otherwise control a user interface 216, and/or a communication interface 218. As such, the processing circuitry 210 may be embodied as a circuit chip (e.g., an integrated circuit chip) configured (e.g., with hardware, software, or a combination of hardware and software) to perform operations described herein.

The processor 212 may be embodied in a number of different ways. For example, the processor 212 may be embodied as various processing means such as one or more of a microprocessor or other processing element, a coprocessor, a controller, or various other computing or processing devices including integrated circuits such as, for example, an ASIC (application specific integrated circuit), an FPGA (field programmable gate array), or the like. Although illustrated as a single processor, it will be appreciated that the processor 212 may comprise a plurality of processors. The plurality of processors may be in operative communication with each other and may be collectively configured to perform one or more functionalities of apparatus 200 as described herein. The plurality of processors may be embodied on a single computing device or distributed across a plurality of computing devices collectively configured to function as network 10, client device 30, server 40, database 50, user interface applications 100, save wizard engine 110 and/or apparatus 200. In some example embodiments, the processor 212 may be configured to execute instructions stored in the memory 214 or otherwise accessible to the processor 212. As such, whether configured by hardware or by a combination of hardware and software, the processor 212 may represent an entity (e.g., physically embodied in circuitry—in the form of processing circuitry 210) capable of performing operations according to embodiments of the present invention while configured accordingly. Thus, for example, when the processor 212 is embodied as an ASIC, FPGA, or the like, the processor 212 may be specifically configured hardware for conducting the operations described herein. Alternatively, as another example, when the processor 212 is embodied as an executor of software instructions, the instructions may specifically configure the processor 212 to perform one or more operations described herein.

In some example embodiments, the memory 214 may include one or more non-transitory memory devices such as, for example, volatile and/or non-volatile memory that may be either fixed or removable. In this regard, the memory 214 may comprise a non-transitory computer-readable storage medium. It will be appreciated that while the memory 214 is illustrated as a single memory, the memory 214 may comprise a plurality of memories. The plurality of memories may be embodied on a single computing device or may be distributed across a plurality of computing devices. The memory 214 may be configured to store information, data, applications, computer program code, instructions and/or the like for enabling apparatus 200 to carry out various functions in accordance with one or more example embodiments. For example, when apparatus 200 is implemented as apparatus 200, memory 214 may store data records associated with simulated requests and responses.

The memory 214 may be configured to buffer input data for processing by the processor 212. Additionally or alternatively, the memory 214 may be configured to store instructions for execution by the processor 212. In some embodiments, the memory 214 may include one or more databases, such as database 50, that may store a variety of files, contents, or data sets. Among the contents of the memory 214, applications may be stored for execution by the processor 212 to carry out the functionality associated with each respective application. In some cases, the memory 214 may be in communication with one or more of the processor 212, user interface 216, and/or communication interface 218, for passing information among components of apparatus 200.

The optional user interface 216 may be in communication with the processing circuitry 210 to receive an indication of a user input at the user interface 216 and/or to provide an audible, visual, mechanical, or other output to the user. As such, the user interface 216 may include, for example, a keyboard, a mouse, a joystick, a display, a touch screen display, a microphone, a speaker, and/or other input/output mechanisms. As such, the user interface 216 may, in some example embodiments, provide means for user control of managing data access operations and/or the like. In some example embodiments in which apparatus 200 is embodied as server 40, database 50, save wizard engine 110, and/or the like, aspects of user interface 216 may be limited or the user interface 216 may not be present.

The communication interface 218 may include one or more interface mechanisms for enabling communication with other devices and/or networks. In some cases, the communication interface 218 may be any means such as a device or circuitry embodied in either hardware, or a combination of hardware and software that is configured to receive and/or transmit data from/to a network and/or any other device or module in communication with the processing circuitry 210. By way of example, the communication interface 218 may be configured to enable communication amongst client device 30, server 40, database 50, apparatus 200, and/or the like over a network. Accordingly, the communication interface 218 may, for example, include supporting hardware and/or software for enabling wireless and/or wireline communications via cable, digital subscriber line (DSL), universal serial bus (USB), Ethernet, or other methods.

The network, such as network 10, in which apparatus 200 and/or any of the components described herein may operate may include a local area network, the Internet, any other form of a network, or in any combination thereof, including proprietary private and semi-private networks and public networks. The network may comprise a wired network and/or a wireless network (e.g., a cellular network, wireless local area network, wireless wide area network, some combination thereof, and/or the like).

FIG. 4 is a flowchart illustrating example operations of an apparatus 200 according to some example embodiments. The operations of FIG. 4 may be performed by apparatus 200 (e.g., save wizard engine 110) to track state data of objects in a session and save the data to the database 50. In particular, example embodiments provide a reusable interface that can be accessed by various user interface applications 100, such as those operative on server 40. Example embodiments maintain the data as provided by the interfacing user interface application 100, and transmit consolidated data to the database 50.

As used herein, a session may be considered a series of communications between a client device 30 and server 40. The session may begin when the client device 30 initially accesses an application operative on server 40, such as user interface application 100. The session may end when the user initiates to commit the data to the database 50, such as by selecting "save," "submit," or any similar input component. As another example, the session may end when a user closes the browser. In some examples, a session may include the exchange of data provided via a series of user interface displays, and the user may navigate back and forth between displays, and make configure the data accordingly.

As shown by operation 400, apparatus 200 may include means, such as save wizard engine 110, processor 212, memory 214, user interface 216, communication interface 218, and/or the like, for receiving an indication of a user interface operation based on a user input to a user interface. The user interface operation may be received from a user interface application 100 that invokes the save wizard engine 110, and may include data to be added to, modified on, or deleted from a database. In particular, the user interface operation may pass as a parameter to the save wizard engine 110 a reference or pointer to a record or an object that represents a record. The referenced object may represent a record that is to be modified, added, or deleted in the database 50 as provided by the user interface application 100. In this regard, the data referenced by the temporary data of the save wizard engine 110 may be referred to herein as records or objects. The objects or records may comprise data that when processed can be inserted into an associated database table.

In some embodiments, the user interface operation may also pass as a parameter a flag indicating the type of operation to be performed on the referenced object. For example, the parameters may include a NewOrModified flag or a Deleted flag. Additionally or alternatively, in some embodiments, the user interface application 100 may invoke separate methods depending on whether the data is NewOrModified or Deleted. The NewOrModified and Deleted flags or operations are described in further detail below.

The user interface operation and any parameters associated therewith may be communicated to example embodiments following user entry into or manipulation of fields displayed on the user interface 216. For example, a user may enter data for input to an application, and select a "next" button or similar indicator to continue through various pages of the application. The user interface application 100 may invoke the save wizard engine 110 as the data is entered, and/or as the user continues to a different page or display.

As shown by operation 402, apparatus 200 may include means, such as save wizard engine 110, processor 212, memory 214, user interface 216, communication interface 218, and/or the like, for processing the user interface operation to generate temporary data, wherein the temporary data is categorized as at least one of an insert object, update object or delete object and comprises a reference or pointer to an object or record that is to be added, modified or deleted from the database 50. The term 'temporary data' is used to indicate that the reference or pointer to the data is stored or saved for local access by the save wizard engine 110 and/or apparatus 200, such as in memory 214, but is not yet saved to database 50. In some embodiments, the records or objects referenced by the temporary data may not be available to other applications since it is not yet saved to the database. However, save wizard engine 110 may track and maintain the data for use within the session and may efficiently save the appropriate data to the database at the end of the session.

As introduced above, the data transmitted by the user interface application 100 to the save wizard engine 110 via the user interface operation may include a Deleted flag or a NewOrModified flag. In this regard, the user interface application 100 does not need to track or indicate that the data is new or modified, but rather provides references to the current data, (e.g., currently known to the user interface application 100 taking into consideration the user configurations). Said differently, data flagged as NewOrModified may not yet exist in the database 50, or maybe associated with an existing record in the database 50, but the user interface application 110 does not need to distinguish between the two states of new or modified. The save wizard engine 110 handles the operations and state tracking of the data provided by the user interface application 110 relative to the state of the database.

The save wizard engine 110 may process the operations and the references to data to determine any number of insert operations, update operations, and/or deletion operations that would be made to the database 50 if the data provided in the user interface operation were committed, or saved, to the database. To track the state data, the save wizard engine 110 may maintain a new bucket, update bucket and/or delete bucket during the session, and update the temporary data comprising references or pointers to records or objects stored therein as additional user interface operations are performed in the session. Each of the buckets may be implemented as any data structure configured to store references to any type objects or records provided by the user interface application 100.

According to example embodiments, the referenced objects may comprise record identifiers (e.g., keys) used to uniquely identify the associated record in the database. Accordingly, an object or record referenced in the update and/or delete buckets may be associated with a record identifier linking the data to the database.

In some examples, objects referenced in the new bucket may not have a record identifier associated with the object because the record does not yet exist in the database.

Because the user interface application 100 only needs to flag data as Deleted or NewOrModified, the user interface application 100 may transmit a reference or pointer to any modified object to save wizard engine 110 whether the record is new to the save wizard engine 110 or already exists in one of the buckets. The user interface application 100 does not need to track whether the record is new or modified, but rather provides a reference to the complete record as currently provided in the user interface application 100 to the save wizard engine 110.

If the user interface operation indicates to the save wizard engine 110 that associated data is NewOrModified and the referenced object includes a record identifier linking the record to an existing record in the database, the save wizard engine 110 generates an update object to store in the update bucket. The update object may include a reference to the object which represents the record in the database. In some embodiments, the save wizard engine 110 may store a map that maps record identifiers recognized or recognizable by the database to the associated object in the temporary data. This may allow for improved efficiency so that the save wizard engine 110 does not need to check every object referenced in the temporary data to determine whether the temporary data already references the record. The save wizard engine 110 may instead access the map to determine whether the temporary data already references the associated record, and may only continue to check other objects referenced in temporary data, as described below, if the record is not referenced in the temporary data.

If the user interface operation indicates to the save wizard engine 110 that associated data is NewOrModified, and the referenced object does not include a record identifier linking the record to the database, the save wizard engine 110 may compare the record or object referenced by the user interface operation to those already referenced by the temporary data maintained by the save wizard engine 110 to determine if the save wizard engine 110 already includes temporary data referencing the record. Based on the comparison, the user interface operations may be processed as follows.

If the user interface operation indicates to the save wizard engine 110 that associated data is NewOrModified, and the associated object is not already referenced in the temporary data, (and does not have an associated record identifier linking it to the database), save wizard engine 110 adds an insert object to the new bucket. The insert object may include a reference or pointer to the object representing the new record to be inserted. In this regard, the save wizard engine 110 may generate an insert object which references data to be inserted in various fields of the database table in a new record when the session is complete, as described below with respect to operation 408.

If data received by the save wizard engine 110 is flagged as NewOrModified, does not have an associated record identifier recognized by the database, and it is not new to the save wizard engine 110 (e.g., is already referenced in the new bucket or update bucket) the save wizard engine 110 prevents addition of duplicate references to the temporary data. Said differently, the save wizard engine 110 may ignore the user interface operation, because the referenced object has already been modified by the user interface application 100 and the temporary data of the save wizard engine 110 already references the object. In this regard, as requests are received from the user interface application 100, for a NewOrModified operation, the save wizard engine 110 determines existence of a record in temporary data (e.g., a bucket) by comparing the record being provided against all records referenced in any of the buckets.

In some embodiments, user interface application 100 can transmit a deleted object to the save wizard engine 110 without having to determine if the record exists in the database. If data received by the save wizard engine 110 is flagged as Delete, but the save wizard engine 110 determines the record was newly created in the session and does not yet exist in the database 50 (e.g., does not have an associated record identifier), the save wizard engine 110 may remove the reference to the associated insert object from the new bucket and ignore the associated record. In contrast, if the record does exist in the database (e.g., has an associate record identifier), the save wizard engine 110 may add a delete object to the delete bucket and remove an associated record from the update bucket, if one exists.

In some examples, a user interface operation transmitted to the save wizard engine 110 may be processed such that more than one database operation would be initiated to complete the request. In this regard, references to multiple objects could be added to any of the temporary data buckets for a single user interface operation. For example, a user may provide data associated with the addition of several new database records, possibly in different database tables. As another example, a user may complete a task which results in user interface operations to add a new record, delete an existing record and/or update an existing record. These tasks may be completed on a single user interface display and transmitted to apparatus 200.

As shown by operation 404, apparatus 200 may include means, such as save wizard engine 110, processor 212, memory 214, user interface 216, communication interface 218, and/or the like, for updating the temporary data according to subsequently received indications of user interface operations. In this regard, user interface operations may be interpreted by the save wizard engine 110 and maintained accordingly so as to minimize or reduce database operations ultimately initiated by the save wizard engine 110.

In some embodiments, the save wizard engine 110 may identify that data passed from the user interface application 100 utilizes a different variable that actually points to the same record referenced by the temporary data stored by the save wizard engine 110. In this regard, the following computer program code may return true if the two pointers or references point to the same object. "objectReference1==objectReference2." ObjectReference1 could be a reference provided by the user interface application 100 and objectReference2 could be a reference to the object in one of the buckets of temporary data. If a user is operating on a single object or record, the object pointer that the user interface application 100 passes to the save wizard engine 110 and the record already referenced in the temporary data are pointing to the same object.

For example, consider that a user previously initiated creation of a new record for a patient with a first name of "John," last name of "Doe," and birth date of "mm/dd/yyyy." This data may be referenced by the save wizard engine 110 as an insert object in the new bucket. While entering additional detail on a subsequent page, such as address and phone number, the user may realize the patient's last name is spelled incorrectly. The user may return to the previous page to correct the spelling.

In this regard, the save wizard engine 110 may ignore the subsequent request because the insert object in the new bucket already includes a reference to the same object. Example embodiments may therefore reduce unnecessary database calls to be subsequently made, in comparison to a system that would perform the database insert operation with the misspelled name, followed by an additional database update operation to correct the name.

As another example, a user that creates data that could result in a new record, may ultimately cancel the transaction or delete the instance of the data in the session. In this regard, temporary data stored by the apparatus 200 in the new bucket may be deleted from the new bucket prior to committing the data to the database. In this example, an unnecessary insert and delete operation could be avoided.

As another example, save wizard engine 110 may determine a user interface operation is indicative of a delete operation of a record associated with an object stored in the update bucket. In this regard, the save wizard engine 110 may remove the update object from the update bucket so that the data is not unnecessarily updated prior to deletion, and add a delete object to the delete bucket. If a delete request is associated with a new object (e.g., the object being deleted matches an object saved in the new bucket), the save wizard engine 110 may remove the new object and ignore the delete request, so that the data is not transmitted to the database and subsequently deleted. Instead, the data created and deleted within the session can be ignored by the save wizard engine 110.

In some examples, for each request from the user interface application, example embodiments may search the existing temporary data to determine if the existing temporary data needs to be updated instead of generating new instances of insert objects, update objects, and/or delete objects for every request by default. In some instances the save wizard engine 110 may ignore user interface operations if the object is already referenced by the temporary data As shown by operation 406, apparatus 200 may include means, such as save wizard engine 110, processor 212, memory 214, user interface 216, communication interface 218, and/or the like, for receiving a commit indication indicating to commit the user interface operations (e.g., the data associated with the referenced objects) to the database. The commit indication may be generated in response to a user selecting a "save," or "submit" button. As another example, the commit indication may be generated by any other type of user input, such as the session ending.

As shown by operation 408, apparatus 200 may include means, such as save wizard engine 110, processor 212, memory 214, communication interface 218, and/or the like, for in response to the commit indication, transmitting data referenced by the temporary data to the database with operations associated with each of the respective insert objects, update objects and delete objects. In this regard, example embodiments may traverse the insert objects, update objects, and delete objects and generate database commands representing each of the objects. For example, the commands may be generating in a Structured Query Language (SQL) or other programming language configured to update a relational database such as database 50.

In some embodiments, save wizard engine 110 may therefore determine an order in which database operations will be performed based on dependencies of objects in the temporary data. Accordingly, some database operations may be dependent on other database operations. For example, a new record may be referenced in an update object relating to another record. This scenario may occur, for example, if a user could provide details of a new patient that is a family member of an existing patient and the two patients are to be linked. The save wizard engine 110 may first perform the insert operation relating to the new patient and receive a new record identifier from the database 50. The save wizard engine 110 may then update the record of the existing patient to link to the new patient based on a record identifier returned from the database. In some embodiments, the save wizard engine 110 does not handle the ordering of the database operations, and another component or routine, such as one operative on server 40, may perform other routines to ensure relational database integrity after the save wizard engine 110 transmits the data to the database 50. For example, the user interface application 100 may perform data integrity verification.

Example embodiments described herein provide many technical advantages to the various components of the respective systems. The operations provided above, such as those described with respect to FIG. 4, may be provided by an API configured for reuse. In this regard, save wizard engine 110 may be implemented at least partially as a reusable set of computer program instructions compatible with a plurality of object types. Multiple different user interface applications 100 may therefore employ example embodiments to direct the save wizard engine 110 to track the state data of objects during a session and save the data to the database when the session is complete. As additional user interface applications are implemented, such as on server 40, and/or additional database tables are added to database 50, the API provided by example embodiments may continue to be utilized by application developers to track the state data during a session for subsequent updating to the database.

Further, example embodiments may minimize or reduce a number of database calls, in comparison to other implementations that do not track state data during the session, or those that make database calls as the user interface operations are processed throughout the session. The number of operations performed by server 40 and/or database 50 may therefore be limited or reduced such that processing resources are conserved. Accordingly, performance of the server 40 and/or database 50 may be improved in comparison to other implementations. Example embodiments may therefore minimize or reduce server load, database timeouts, and unnecessary network traffic, and improve performance on the server and database, and throughout the system.

Similarly, due to the minimized or reduced number of database operations, example embodiments also provide for cleaner audit records relative to other implementations, such that clear and concise audit trails of updates to the database can be stored for subsequent review and audit.

It will be appreciated that the figures are each provided as examples and should not be construed to narrow the scope or spirit of the disclosure in any way. In this regard, the scope of the disclosure encompasses many potential embodiments in addition to those illustrated and described herein. Numerous other configurations may also be used to implement embodiments of the present invention.

FIG. 4 illustrates operations of a method, apparatus, and computer program product according to some example embodiments. It will be understood that each operation of the flowcharts or diagrams, and combinations of operations in the flowcharts or diagrams, may be implemented by various means, such as hardware and/or a computer program product comprising one or more computer-readable mediums having computer readable program instructions stored thereon. For example, one or more of the procedures described herein may be embodied by computer program instructions of a computer program product. In this regard, the computer program product(s) which embody the procedures described herein may comprise one or more memory devices of a computing device (for example, memory 214) storing instructions executable by a processor in the computing device (for example, by processor 212). In some example embodiments, the computer program instructions of the computer program product(s) which embody the procedures described above may be stored by memory devices of a plurality of computing devices. As will be appreciated, any such computer program product may be loaded onto a computer or other programmable apparatus (for example, apparatus 200) to produce a machine, such that the computer program product including the instructions which execute on the computer or other programmable apparatus creates means for implementing the functions specified in the flowchart block(s). Further, the computer program product may comprise one or more computer-readable memories on which the computer program instructions may be stored such that the one or more computer-readable memories can direct a computer or other programmable apparatus to function in a particular manner, such that the computer program product may comprise an article of manufacture which implements the function specified in the flowchart block(s). The computer program instructions of one or more computer program products may also be loaded onto a computer or other programmable apparatus (for example, apparatus 200 and/or other apparatus) to cause a series of operations to be performed on the computer or other programmable apparatus to produce a computer-implemented process such that the instructions which execute on the computer or other programmable apparatus implement the functions specified in the flowchart block(s).

Accordingly, blocks of the flowcharts support combinations of means for performing the specified functions and combinations of operations for performing the specified functions. It will also be understood that one or more blocks of the flowcharts, and combinations of blocks in the flowcharts, can be implemented by special purpose hardware-based computer systems which perform the specified functions, or combinations of special purpose hardware and computer instructions.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

That which is claimed:

1. A method for tracking state data of objects during a session for updating a database, the method comprising:
   receiving a first indication of a first user input to a user interface;
   based on the first user input, generating a first user interface operation that includes a first flag indicating the first user interface operation indicates a new data record or a modified data record, and
   a first reference to a first referenced object, wherein the first referenced object includes a record identifier;
   processing the first user interface operation to at least one of generate or update temporary data, wherein the temporary data includes an insert object based on the first user interface operation;
   receiving a second indication of a second user input to the user interface;
   based on the second user input, generating a second user interface operation that includes
   a second flag indicating the second user interface operation indicates deletion of a data record from the temporary data, and
   a second reference to a second referenced object; and
   processing the second user interface operation to update the temporary data, wherein the temporary data includes a delete object based on the second user interface operation, and wherein processing the second user interface operation comprises, determining whether the second reference to the second referenced object of the second user interface operation includes a reference to the first referenced object of the first user interface operation, responsive to a determination that the second reference to the second referenced object of the second user interface operation includes the reference to the first referenced object of the first user interface operation, removing the insert object from the temporary data prior to transmitting data referenced by the temporary data to the database;
   wherein the tracking of the state data is performed by a reusable set of computer program instructions configured as an application program interface (API) compatible with a plurality of object types and a plurality of database tables; and
   wherein processing the second user interface operation further comprises, determining whether the second referenced object includes a record identifier associated with the database, responsive to a determination that the second referenced object includes the record identifier associated with the database, removing an update object from the temporary data, wherein the update object includes a reference to a referenced object that includes the record identifier associated with the database.

2. The method of claim 1, wherein processing the second user interface operation further comprises removing an update object from the temporary data, wherein the update object includes a reference to the first referenced object of the first user interface operation.

3. The method of claim 1, wherein the temporary data including the insert object based on the first user interface operation comprises the temporary data including a plurality of insert objects based on the first user interface operation.

4. The method of claim 1, further comprising:
maintaining a map that maps record identifiers recognizable by the database to associated objects in the temporary data.

5. The method of claim 1, wherein the first flag does not distinguish whether the first referenced object is new or modified.

6. The method of claim 1, further comprising:
updating the temporary data according to subsequently received indications of user interface operations;
receiving a commit indication indicating to commit the first user interface operation, the second user interface operation, and the subsequently received user interface operations to the database; and
in response to the commit indication, transmitting data referenced by the temporary data to the database with operations associated with each of the respective insert objects and delete objects.

7. The method of claim 6, wherein:
transmitting the data referenced by the temporary data to the data with operations associated with each of the respective insert and delete objects comprises determining an order in which the database performs the operations; and
determining the order in which the database performs the operations is based on dependencies of objects in the temporary data.

8. An apparatus for tracking state data of objects during a session for updating a database, the apparatus comprising at least one processor and at least one memory including computer program code, the at least one memory and the computer program code configured to, with the processor, cause the apparatus to at least:
receive a first indication of a first user input to a user interface;
based on the first user input, generate a first user interface operation that includes
a first flag indicating the first user interface operation indicates a new data record or a modified data record, and
a first reference to a first referenced object, wherein the first referenced object includes a record identifier;
process the first user interface operation to at least one of generate or update temporary data, wherein the temporary data includes an insert object based on the first user interface operation;
receive a second indication of a second user input to the user interface;
based on the second user input, generate a second user interface operation that includes
a second flag indicating the second user interface operation indicates deletion of a data record from the temporary data, and
a second reference to a second referenced object; and
process the second user interface operation to update the temporary data, wherein the temporary data includes a delete object based on the second user interface operation, and wherein processing the second user interface operation comprises, determining whether the second reference to the second referenced object of the second user interface operation includes a reference to the first referenced object of the first user interface operation, responsive to a determination that the second reference to the second referenced object of the second user interface operation includes the reference to the first referenced object of the first user interface operation, removing the insert object from the temporary data prior to transmitting data referenced by the temporary data to the database;
wherein the tracking of the state data is performed by a reusable set of computer program instructions configured as an application program interface (API) compatible with a plurality of object types and a plurality of database tables; and
wherein processing the second user interface operation further comprises, determining whether the second referenced object includes a record identifier associated with the database, responsive to a determination that the second referenced object includes the record identifier associated with the database, removing an update object from the temporary data, wherein the update object includes a reference to a referenced object that includes the record identifier associated with the database.

9. The apparatus of claim 8, wherein processing the second user interface operation further comprises removing an update object from the temporary data, wherein the update object includes a reference to the first referenced object of the first user interface operation.

10. The apparatus of claim 8, wherein the temporary data including the insert object based on the first user interface operation comprises the temporary data including a plurality of insert objects based on the first user interface operation.

11. The apparatus of claim 8, the at least one memory and the computer program code are further configured to, with the processor, cause the apparatus to:
maintain a map that maps record identifiers recognizable by the database to associated objects in the temporary data.

12. The apparatus of claim 8, wherein the first flag does not distinguish whether the referenced object is new or modified.

13. The apparatus of claim 8, the at least one memory and the computer program code are further configured to, with the processor, cause the apparatus to:
update the temporary data according to subsequently received indications of user interface operations;
receive a commit indication indicating to commit the first user interface operation, the second user interface operation, and the subsequently received user interface operations to the database; and
in response to the commit indication, transmit data referenced by the temporary data to the database with operations associated with each of the respective insert objects and delete objects.

14. A computer program product for tracking state data of objects during a session for updating a database, the computer program product comprising at least one non-transitory computer-readable storage medium having computer-executable program code instructions stored therein, the computer-executable program code instructions comprising program code instructions to:

receive a first indication of a first user input to a user interface;

based on the first user input, generate a first user interface operation that includes a first flag indicating the first user interface operation indicates a new data record or a modified data record, and a first reference to a first referenced object, wherein the first referenced object includes a record identifier;

process the first user interface operation to at least one of generate or update temporary data, wherein the temporary data includes an insert object based on the first user interface operation;

receive a second indication of a second user input to the user interface;

based on the second user input, generate a second user interface operation that includes a second flag indicating the second user interface operation indicates deletion of a data record from the temporary data, and a second reference to a second referenced object; and process the second user interface operation to update the temporary data, wherein the temporary data includes a delete object based on the second user interface operation, and wherein processing the second user interface operation comprises, determining whether the second reference to the second referenced object of the second user interface operation includes a reference to the first referenced object of the first user interface operation, responsive to a determination that the second reference to the second referenced object of the second user interface operation includes the reference to the first referenced object of the first user interface operation, removing the insert object from the temporary data prior to transmitting data referenced by the temporary data to the database;

wherein the tracking of the state data is performed by a reusable set of computer program instructions configured as an application program interface (API) compatible with a plurality of object types and a plurality of database tables; and wherein processing the second user interface operation further comprises, determining whether the second referenced object includes a record identifier associated with the database, responsive to a determination that the second referenced object includes the record identifier associated with the database, removing an update object from the temporary data, wherein the update object includes a reference to a referenced object that includes the record identifier associated with the database.

15. The computer program product of claim 14, the computer-executable program code instructions further comprising program code instructions to:

update the temporary data according to subsequently received indications of user interface operations;

receive a commit indication indicating to commit the first user interface operation, the second user interface operation, and the subsequently received user interface operations to the database; and in response to the commit indication, transmit data referenced by the temporary data to the database with operations associated with each of the respective insert objects and delete objects.

* * * * *